United States Patent [19]

Ruijten et al.

[11] Patent Number: 4,554,071
[45] Date of Patent: Nov. 19, 1985

[54] PRE-COLUMN FOR PRECONCENTRATING SUBSTANCES TO BE CHROMATOGRAPHED AS WELL AS DEVICE FOR A LIQUID CHROMATOGRAPHY SYSTEM AND COUPLING MEMBER FOR SAID DEVICE

[75] Inventors: Henri M. Ruijten; Hans De Bree; Peter H. Van Amsterdam; Elbert Wiegers, all of Weesp, Netherlands

[73] Assignee: Duphar International Research B.V., Weesp, Netherlands

[21] Appl. No.: 648,358

[22] Filed: Sep. 7, 1984

Related U.S. Application Data

[63] Continuation of Ser. No. 488,167, Apr. 25, 1983, abandoned.

[30] Foreign Application Priority Data

Apr. 28, 1982 [NL] Netherlands ................. 8201757

[51] Int. Cl.⁴ ............................................. B01D 15/08
[52] U.S. Cl. ................................... 210/198.2; 55/386
[58] Field of Search ................. 210/656, 198.2; 55/67, 55/386, 197

[56] References Cited

U.S. PATENT DOCUMENTS

| | | | |
|---|---|---|---|
| 3,578,785 | 5/1971 | Patterson | 210/198.2 |
| 3,782,078 | 1/1974 | Jerpe | 210/198.2 |
| 4,070,284 | 1/1978 | Fujita et al. | 210/198.2 |

*Primary Examiner*—John Adee
*Attorney, Agent, or Firm*—Stevens, Davis, Miller & Mosher

[57] ABSTRACT

The invention relates to a pre-column of pressure-resistant material for preconcentrating at elevated pressure substances to be chromatographed, which column consists of a vessel-shaped body which narrows internally towards the two ends and has means for sealing connections, upstream to an inlet tube for the liquid to be preconcentrated and downstream to a separating column.

The invention also relates to a device for a liquid chromatography system, comprising one or more pre-columns, optionally one or more separating columns, and a coupling member, and to a coupling member for said device.

9 Claims, 14 Drawing Figures

PRE-COLUMN FOR PRECONCENTRATING SUBSTANCES TO BE CHROMATOGRAPHED AS WELL AS DEVICE FOR A LIQUID CHROMATOGRAPHY SYSTEM AND COUPLING MEMBER FOR SAID DEVICE

This application is a continuation of application Ser. No. 488,167, filed Apr. 25, 1983 abandoned.

The invention relates to a pre-column of pressure-resistant material for preconcentrating at elevated pressure substances to be chromatographed. The invention further relates to a device for a liquid chromatography system and to a coupling member for said device.

Liquid chromatography is a much used separation technique, both for tracing and subsequent identification and determination of the concentrations of substances dissolved or dispersed in liquids, and for separating on a preparative scale of these substances from liquids. In the former case we have analytical, in the latter case preparative liquid chromatography. Liquid chromatography (LC), in particular the so-called "high performance liquid chromatography" (HPLC) may be distinguished into liquid-solid chromatography (LSC), partition chromatography, such as liquid-liquid chromatography (LLC) and bounded-phase chromatography (BPC), ion exchange chromatography, affinity chromatography, and exclusion chromatography, such as gel permeation (GPC) and gel filtration chromatography.

In most of these chromatographic techniques, one or more columns are used which are filled with a, usually granular, carrier material. The choice of the carrier material depends on the material to be chromatographed, on the liquid in which said material is present, and on the solvents which are used in the chromatographic process. The choice of the solvents and carrier to be used is thus determined by the separation problem which is to be solved.

When the substances to be separated or detected are present in the liquid in traces, i.e. in very small concentrations, it is usual to use a preconcentration. In this case a preconcentration column or pre-column is often used which can be connected before the actual chromatography column or separation column. Such a pre-column ("concentration column") to be used in liquid chromatography is described in U.S. Pat. No. 4.070.284. The cylindrical column described has a maximum size of 0.4 inches in diameter and 0.6 inches in length, and a resistance to pressure of 3 MPa at most. Such a column, however, is not suitable for most of the purposes described before, for example for preconcentrating medicaments and/or metabolites thereof in body fluids with the use of HPLC, because both the capacity and the resolution are too small. The use of a column packing with a relatively large particle size as recommended in the patent, apparently to avoid an inadmissible increase of pressure during the preconcentration process, even has an unfavourable influence on the resolution. The use of a pre-column in the HPLC technique is described, for example, by Roth c.s. in J. Chrom. 222, (1981), pp. 13-22. This article relates to the tracing of medicaments or metabolites hereof in body fluids. The concentration of these trace components in body fluids is very low, for example, in the order or nanogrammes per ml, so that a preconcentration is necessary. The pre-columns used by Roth c.s. are straight columns, 25 mm long, filled dry with a carrier suitable for the intended application. A sample of the body fluid to be examined is provided hereon, the trace components to be detected being adsorbed on the carrier material. The trace components are then eluted from the pre-column or the sepration column with a solvent chosen for this purpose. The chromatography column or separation column is filled with a carrier material which is suitable for separating the trace components in the various constituents. By elution of the separation column, the components can be collected and detected in a more or less pure condition.

It has been found, however, that, when a straight pre-column is used, as described, for example, by Roth c.s. in the above article, the actual separation of the material adsorbed in the pre-column into the various constituents by means of one or more separation columns is disturbed. As a matter of fact, in the subsequent elution, clogging and ghost effects occur as a disturbing factor, while the resolution usually is bad. Similar phenomena which occur in particular when chromatographing larger volumes have also been established by Schauwecker c.s.: J. Chrom. 136, (1977), 65.

It has now been found, however, that the abovementioned problems do not occur when for the preconcentration a pre-column is used which consists of a vessel-shaped body which narrows internally towards the two ends and has means for sealing connections, upstream to an inlet tube for the liquid to be preconcentrated, and downstream to a separation column. When such a pre-column is used it has proved possible to preconcentrate traces of metabolites and the like present in body fluids in such manner that in the subsequent separation on the chromatography column the disturbing ghost effects and poor resolution do not occur.

The pre-column according to the invention permits of performing a preconcentration of various body fluids, such as urine, lumbar fluid, saliva and blood plasma, but also of homogenates of organs and of faeces. As a result of this it is possible to detect and determine traces of medicaments and of metabolites in these fluids and excreta, and even to isolate them. The pre-column according to the invention, however, is not destined only for a pharmaceutical or clinical use, but may also be used in all other fields where trace analyses have to be carried out, for example in the analysis of waste water, drinking water, rain water, ground water and surface water, both quantitatively and qualitatively, and in the detection, determination and isolation of metabolites of, for example, pesticides in crops, in the soil, in the ground water and in the surface water.

On the basis of theoretical considerations, Said (J. High Res. Chrom. Commun. Feb. 1979, pp. 63-67) has come to the recognition that for a chromatography column or separation column a conical shape is to be preferred to a step-wise composed (composite) shape. However, this theoretical consideration -which otherwise relates to a separation problem and not to a preconcentration problem, is not concretized by any practical example. Otherwise, the dimensions of a chromatography column cannot be used as such for a preconcentration column, because these are determined inter alia by the object for which the column is developed. This also appears from the theoretical preferred model of the separation column drawn by Said which has a conical variation from a diameter of 3 cm to one of 1 cm over a length of 1 m. Such dimensions are not suitable for a pre-column. As a matter of fact, the contents of the pre-column may not be too large for an effective preconcentration. Otherwise, the concentration of the trace components in the eluent during the separation would become too low to enable an accurate detection and measurement. Therefore, the length of the pre-column is preferably not more than approximately 10 cm, but the inlet and outlet apertures must be sufficiently wide to avoid too high a pressure build-up in the column. In addition, the pre-column according to the invention serves for the preconcentration at elevated pressure, i.e. it must be used at pressures between 100 kPa and 10 MPa which are usual for this application. In Said's consideration such pressures are not taken into account. During the separation process, so when the pre-column is connected to a separation column, the pressure in the pre-column can even rise to approximately 40 MPa. In designing a column, such high pressures will no doubt have to be taken into account. The shape of the column will therefore have to be suitable not only to be able to preconcentrate the substances to be chromatographed while avoiding the above-described phenomena occurring during the elution, but also to be able to withstand pressures up to approximately 40 MPa.

The pre-column can be used for any of the above-mentioned chromatographic separation processes in which a column is necessary, for example, liquid-liquid chromatography (LLC), liquid-solid chromatography (LSC), ion exchange chromatography, affinity chromatography and gel permeation chromatography (GPC).

In a preferred embodiment the pre-column according to the invention has such a shape that the inner wall of the vessel-shaped body converges towards the ends conically or integrally. Preferably the connection means - upstream to an inlet tube for the liquid to be preconcentrated and downstream to a separation column - are present diametrically opposite to each other at the two ends of the vessel-shaped body. These connections may be screw connections or clamping connections which can withdraw a pressure of at least 40 MPa. In a further preferred embodiment the inner wall of the vessel-shaped body narrows more strongly in the direction of the upstream end than in the direction of the downstream end. As a result of this a certain maximum diameter is rapidly reached for the supplied liquid, while the reduction of the maximum column diameter to the diameter of the downstream aperture is more gradual. A further advantage is that the diameter of the downstream aperture of the vessel-shaped body is approximately equal to that of a separation column to be connected to the pre-column, so that the so-called "laminar flow" pattern is disturbed as little as possible when during the chromatographic separation process the pre-column is connected to a separation column. The column which is preferably made of stainless steel, may for formed integral, but it may also be composed of two or more segments which are secured together in a pressure-resistant manner. A suitable connection can be obtained, for example, by externally providing the outer segments with flanges and clamping the flanges together by means of a clamping ring or clamping band or by means of screw bolts through said flanges. If desired, a good pressure-resistant seal can be reached by means of gaskets of a suitable material. From a point of view of production technology, a pre-column of several segments has advantages over a column which is formed integrally; this applies in particular to columns of larger dimensions. As already stated above, the pre-column must be capable of withstanding pressures of at least 40 MPa. This pressure-resistance can be reached more easily by composing the column of several segments.

Before use of the pre-column, the column is filled with a suitable carrier material or adsorption agent. For HPLC examination of body fluids is suitable, for example, pre-treated silica gel, such as silica gel made water-repellent (hydrophobated). For other applications, other carrier materials usual in the liquid chromatographic technique, such as aluminium oxide or ion exchange resins, may also be used. The column may be packed dry with the carrier material, but the carrier may alternatively be provided in the column as a slurry. In the tapering upstream part of the column an inert filler is preferably provided on the carrier material; if hydrophobated silica gel is used as a carrier material, glass beads or silica gel may be used as inert fillers. By the use of an inert filler it is reached that the material to be chromatographed provided on the pre-column is distributed more uniformly entirely across the column. Such a filling is also recommended by de Jong c.s. (J. Chrom. 148 (1978), pp. 127–141). The carrier material is preferably enclosed in the column between two filters, for example, of sintered metal. After the usual conditioning of the pre-column, a sample of the liquid to be examined is applied to the column by means of a tube with connected syringe, or, if larger volumes are concerned, by means of a pump. The adsorbed components remain on the carrier, while the liquid drains the non-adsorbed material through the column; the waste liquid is drained from the column via an outlet tube. The pre-column is then connected downstream to a separation column or chromatography column, which column is also conditioned in the usual manner. The adsorbed material is then eluted in the separation column by means of a suitable solvent or solvent mixture, after which the separation column is eluted preferably with the same solvent or solvent mixture. Instead of an eluent of constant composition, a solvent mixture of continuously varying composition is often used: gradient elution; in addition to a continuous gradient elution, a step-wise gradient elution may also be used. The pressure required for the chromatography process is obtained by using one or more pumps. The liquids chromatograph further comprises the usual control apparatus, an automatic fraction collector and detectors suitable for detecting the constituents to be examined.

The use of a liquid chromatography system as described above entails frequent switching of connections. In fact, the pre-column must first be conditioned and be treated with the liquid to be chromatographed. Both the solution necessary to condition the column and the waste liquid from which the trace components have been removed by adsorption on the carrier, must be drained from the column. Therefore, a connection possibility for an outlet tube is necessary at the downstream end. For the actual separation process (elution) the pre-column must then be connected at the downstream end to a separation column. In order to enable conditioning, the separation column is also provided with a facility for an upstream connection to an inlet tube for liquid. For various purposes, for example for the simultaneous chromatography of more liquid samples, for the repeated preconcentration of column eluates, or for a repetition of the chromatography process with the aim of obtaining a higher degree of purity, it is moreover highly desirable to be able to connect at will several pre-columns to several separation columns.

The invention therefore also relates to a connection system which makes it possible in a simple manner to connect one or more pre-columns at will to an outlet tube for waste liquid or to one or more separation columns. For that purpose a device for a liquid chromatography system was developed which comprises (1) one or more pre-columns, (2) a member for coupling the column or columns and an inlet tube for liquid to one or more separation columns and to an outlet tube for waste liquid, and (3), if desired, one or more separation columns. The pre-columns may be of the type as described above.

A device for a liquid chromatography system is also described in U.S. Pat. No. 4.070.284 mentioned before, which device is provided with some multi-way valves for connecting the pre-column to the separation column. These multi-way valves, however, are not resistant to pressures higher than a few megapascals. As a particular aspect of the invention a coupling member for the above-mentioned device was developed with a pressure-resistance of at least 20 MPa. The coupling member according to the invention comprises two concentric disks which are rotatable relative to each other in a mutually sealing connection, apertures for the sealing connection of the pre-column or columns and an inlet tube for liquid being recessed in one of the disks, apertures for the sealing connection of the separation column or columns and the outlet tube for waste liquid being recessed in the other disk, the apertures in the two disks being made to communicate with each other at will by rotating one disk relative to the other. The disks of the coupling member which are preferably made of stainless steel are sealingly connected together, for example, by means of teflon gaskets. By using gaskets which are circular in cross-section and which are mounted in circumferential grooves recessed in the disks, the disks can rotate relative to each other. The coupling member can withstand a pressure up to approximately 40 MPa. The connections to the apertures in the disks are also made preferably of stainless stell and the sealings of teflon, if desired.

In order to be able to connect the pre-column or pre-columns, the separation column or separation columns and the inlet tubes and outlet tubes to the apertures recessed in the disks, connection means, for example, in the form of screw connections or clamping couplings are present. Another suitable coupling member is formed by an insert having a central bore, which insert fits sealingly, with a column or nipple for inlet or outlet tube connected thereto, in an aperture recessed in one of the disks, the insert being provided externally with a flange which engages a shoulder formed by the recessed aperture in the disk. The central bore in the insert communicates on the outside with a column or nipple which, for example, is welded to the insert or is connected to the insert by means of a screw connection, and on the inside with a narrowed bore in the disk. The diameter of the central bore in the insert is preferably approximately equal to the inside diameter of the column or the nipple. By using columns having inserts of the same outside diameter and external shape, any column can rapidly be connected at will to an associated aperture recessed in one of the disks of the coupling member. In order to be able to easily rotate the disks relative to each other either manually or automatically one disk may be fixed, for example, by clamping a handle connected to the disk in a stand, while the other disk is provided with an auxiliary means to perform the desired rotation. For manual operation of the latter disk, a handle or a connection facility for a handle is preferably provided in the outer edge. The disks may further comprise a locking device, for example, an abutment pin or plate, an abutment pin in a milled groove or a fixing catch or screw which fixes the place in which the apertures in the disks communicate with each other.

The invention will now be described in greater detail with reference to preferred embodiments which are shown in the drawings, in which.

Figure 1:
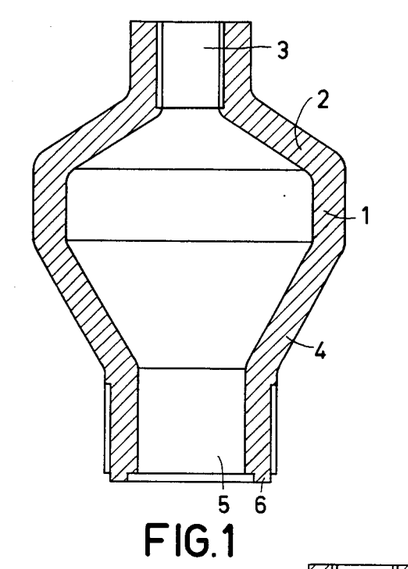
FIGS. 1, 2 and 3 are longitudinal cross-sectional views of pre-columns according to the invention.

The pre-column shown in the longitudinal sectional view of FIG. 1 consists of one assembly and is made of stainless steel. The cylindrical central part 1 converges conically towards the two ends, the part 2 converging more strongly in the direction of the upstream end 3 than the part 4 in the direction of the downstream end 5. The upstream end 3 has internal screwthread into which a nipple having external screwthread can be screwed. An inlet tube for the liquid to be chromatographed can be connected to said nipple. The downstream end has external screwthread with which the pre-column can be screwed into a coupling member, as shown for example in FIG. 6, and has a projecting circumferential edge or ridge 6 which forms a mount for a gasket.

Figure 2:
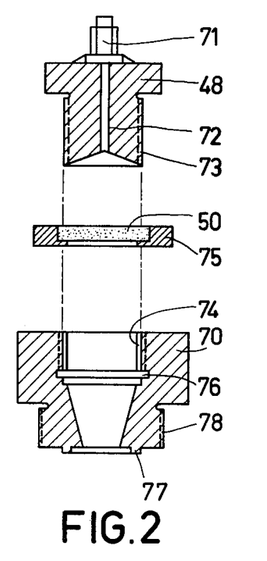
Figure 3:
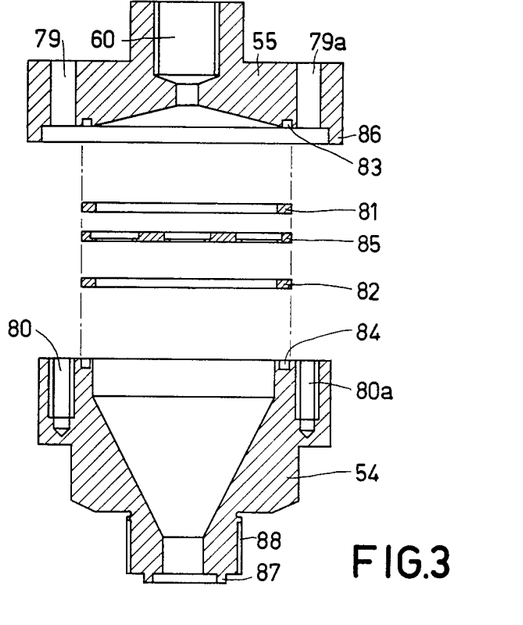
Figure 7:
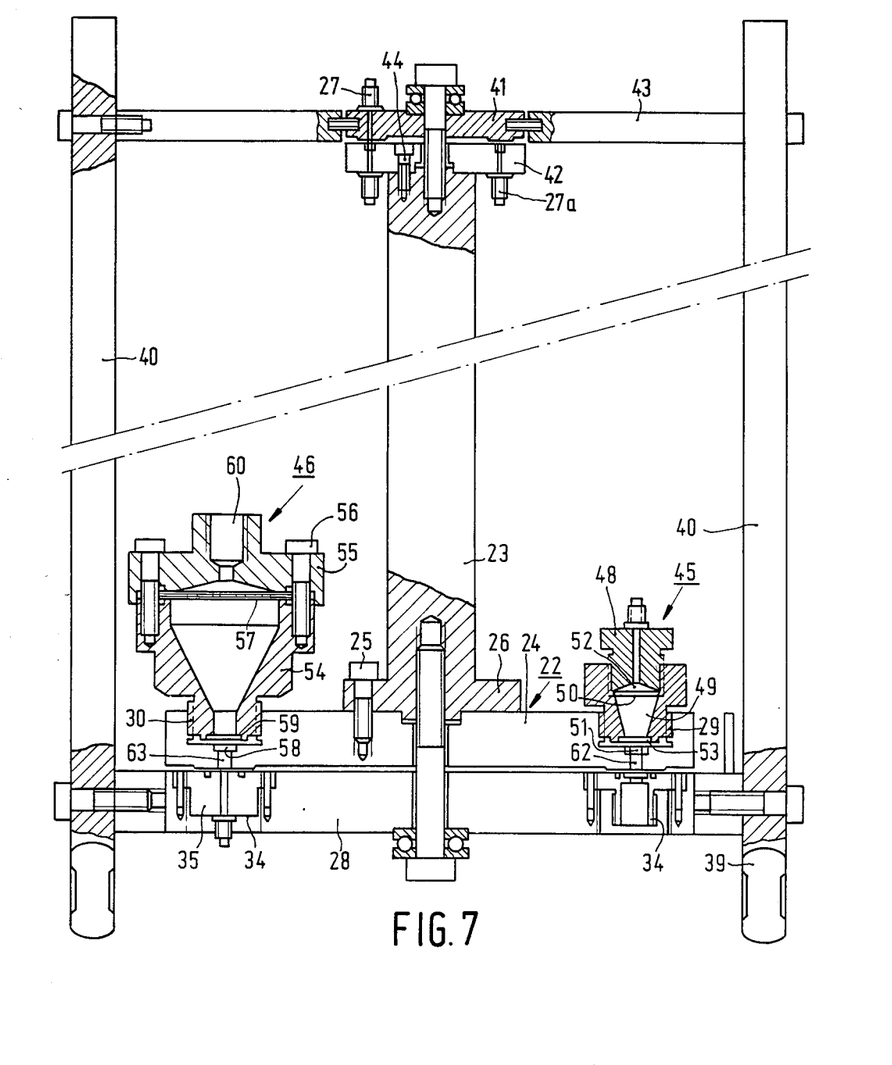
FIG. 7 is a sectional view of a device for a liquid chromatography system having a coupling member and pre-columns in accordance with the invention.
Figure 8:
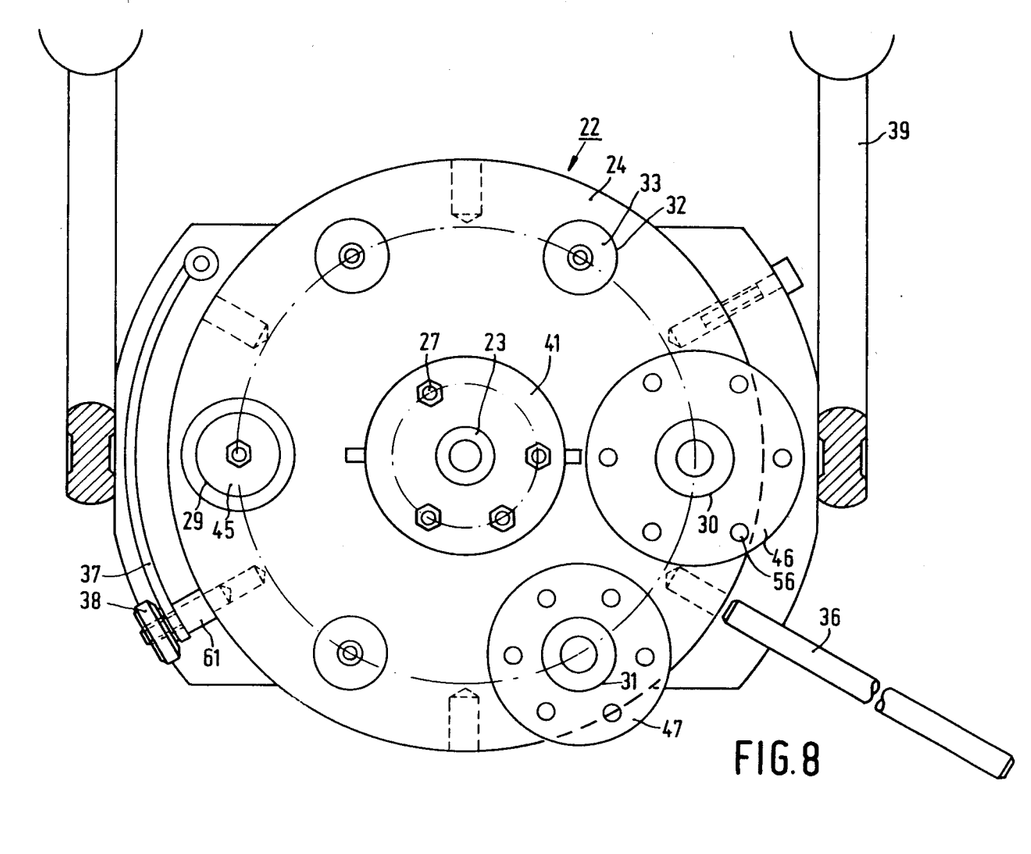
FIG. 8 shows the same device as FIG. 7, this time as a plan view.

FIGS. 2 and 3 are cross-sectional views of pre-columns according to the invention which are composed of two parts, namely vessel-shaped parts 70 and 54, respectively, and covers 48 and 55, respectively. The cover of the pre-column shown in FIG. 2 has a nipple 71 to which an inlet tube can be connected through which liquid can reach the interior of the column via central bore 72. The cover has external screwthread 73 with which it can be screwed into the vessel-shaped part having internal screwthread 74 up to a gasket 75 which fits in a mount 76 of the vessel-shaped part. The gasket 75 in which a filter of sintered metal 50 is mounted, is shown on an enlarged scale in the drawing. The vessel-shaped part 70 at the downstream end has an external circumferential ridge 77 which forms a mount for a gasket, and has screwthread 78 with which the column can be screwed into a coupling member, for example, as shown in FIGS. 7 and 8. Through recesses 79 and 79a in the cover and tap-shaped apertures 80 and 80a in the vessel-shaped part, which apertures have internal screwthread, the parts of the bipartite column shown in FIG. 3 can be screwed one on top of the other by means of bolts. The gaskets 81 and 82 fall into the circumferential grooves 83 and 84 recessed respectively in the cover and vessel-shaped part, while a filter or filters present in a filter holder 85 is or are kept in its or their place between the gaskets. The cover has a circumferential edge 86 which adjoins the outer edge of the vessel-shaped part. An internally screwthreaded connection aperture 60 for a nipple for connection to an inlet tube is present in cover 55. Internally the column tapers conically towards the two ends, towards the upstream end at an angle of 75°, towards the downstream end at an angle of 27°. Finally, the vessel-shaped part of the column at the downstream end again has externally a circumferential ridge 87 and screwthread 88.

Figure 4:
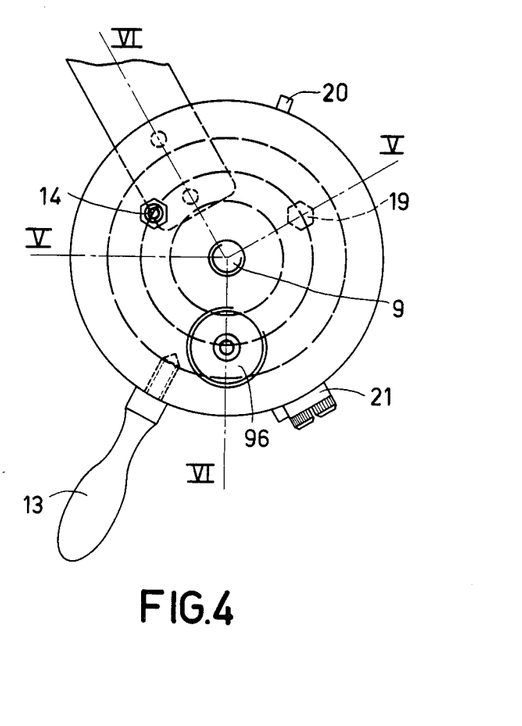
FIGS. 4, 5 and 6 are a plan view and cross-sectional views of a coupling member for a liquid chromatography system.

FIG. 4 is a plan view of a coupling member of a device for a liquid chromatography system to which a pre-column can be connected at 96. As is clearly visible in FIGS. 5 and 6 which are cross-sectional views of the same device taken on the lines V—V and VI—VI, respectively, of FIG. 4, the coupling member comprises two concentric disks 7 and 8, also of stainless steel, disk 7 being rotatable about a bearing boss 9. The disks are clamped one on the other by the same boss 9 which is constructed as a bolt and is screwed through disk 7. Circular gaskets (for example, 10 and 11) of teflon which have an approximately circular cross-section are present between the two disks in grooves recessed in one of the disks. The circular gaskets are present between the disks and are provided around the bores (see hereinafter) in the disks. The connection aperture for the pre-column 96 has external screwthread so that the column can be screwed into it up to a sealing gasket 12 of reinforced teflon. On the other side of the gasket the aperture 96 is narrowed to form a bore having a smaller diameter, while a filter of sintered metal 90 which is disk-shaped is present between the connection aperture and the bore. On the outer edge of the same disk in which the connection aperture for the pre-column is recessed, a handle 13 is provided. Said disk furthermore comprises a nipple 14 for the connection to an inlet tube for conditioning liquid. A conditioning liquid is used to condition the separating column or columns prior to the chromatography process. On the other disk of the coupling member a handle 15 is connected by means of two bolts, which handle can be fixed at its end 16 remote from the disk in a stand. An insert 18 for the connection to a separating column and having a central bore is present in a mount 17 of the same disk. This latter disk moreover comprises a nipple 19 for the connection to an outlet tube for waste liquid. The disk furthermore comprises an abutment plate and pin 20, 21, as a result of which the rotational distance of the disks relative to each other necessary to make the apertures in the disks communicate with each other can more easily be determined.

The device shown in FIGS. 7 and 8 for a liquid chromatography system comprises a coupling member 22 consisting of two concentric stainless steel disks which are rotatable about a shaft 23 which has bearings at each end and in which disks apertures are recessed. The same teflon gaskets are present as described before the FIGS. 4–6 embodiment. The upper disk 24 is connected to a flange 26 of the central shaft 23 by means of bolts 25. The upper disk is rotatable relative to the lower disk, the shaft also rotating. Six apertures are recessed in the upper disk and are provided with screwthread so that either pre-columns (at 29, 30 and 31) or, as at 32, inserts 33 having central bores and comprising nipples or to which nipples can be connected can be screwed into them. All apertures are continued inwardly as bores of reduced diameters. Apertures 34 are also recessed in the lowermost disk and form mounts for inserts 35 which have a central bore and to which nipples or separating columns are or can be connected. The mounts in the disks are of the same shape as those described with reference to FIGS. 4–6. The upper disk can be rotated with respect to the lower disk by means of a handle 36. The lower disk 28 furthermore comprises a locking device for the upper disk 24, comprising a resilient arm 37 having a pawl 61 which falls into apertures recessed in the outer edge of the upper disk. Therewith the upper disk can be fixed in a given position relative to the lower disk. The fixing can be removed by pulling the pawl with the knob 38 against the action of the spring out of an aperture in the outer edge of the upper disk.

At its outer edge the lower disk is screwed into a stand 39, comprising two diametrically oppositely located rod-shaped elements 40 extending parallel to the central shaft 23. At some distance above the coupling member 22, two circular stainless steel plates 41, 42 are connected to the central shaft 23, the uppermost 41 of which being connected to the rod-shaped elements 40 of the stand by means of connection bars or spokes 43. The plates are sealingly clamped one on top of the other, circular teflon gaskets being provided between the plates as was the case with the disks of the coupling member. The lower plate 42 is rigidly secured to the bearing shaft 23 by means of bolts 44, and hence rotates with the upper disk 24 of the coupling member 23. Both plates 41 and 42 comprise nipples 27, 27a which are connected to bores provided in the plates. The nipples in the lower plate 42 can be connected by means of liquid tubes to the nipples or pre-columns in the upper disk 24 of the coupling member 22; the nipples in the upper plate 41 can be connected to reservoirs containing different liquids, for example, conditioning liquid, liquid to be chromatographed and various elution liquids. The device shown in FIGS. 7 and 8 is excellently suitable for an automatic chromatography process, because between conditioning, loading the pre-column or columns with trace components to be separated, and various elutions, no inlet tubes need to be detached. Any desired liquid can be introduced into one of the pre-columns or separating columns by a simple rotation of the upper coupling disk.

In the device shown in FIGS. 7 and 8, three stainless steel pre-columns according to the invention are provided which are screwed into the upper disk 24 of the coupling member 22. The column 45 screwed into aperture 29 of said disk is of the type as shown in FIG. 2. The columns 46 and 47 screwed into the apertures 30 and 31 of disk 24 are of the type shown in FIG. 3. Column 45 comprises a cover 48 having a screw connection and connection nipple. The carrier material is enclosed in the column between two filters 50, 51 of sintered metal. In the conical part of the column on the side of the upstream end, an inert filler 52 is present on the filter. The column is sealingly connected to the elongated bore 62 of the aperture 29 recessed in the upper coupling disk 24 by means of a teflon gasket 53. Column 46 consists of two parts (54 and 55) which are connected together by means of bolts 56. As in column 45, filters of sintered metal 57, 58 are also present in column 46, while the sealing to the upper coupling disk 24 is formed by a teflon gasket 59. The column communicates at the downstream end with aperture 63 in disk 24.

Of course, various modifications of the abovedescribed devices are possible. For example, the number of apertures recessed in the disks of the coupling member and in the circular plates may be varied at will and may be suitable for various connections, for example, inserts or screw connections. Many other modified embodiments obvious to those skilled in the art are also possible without departing from the scope of the present invention.

When using a pre-column according to the invention, first the carrier material, for example a hydrophobated silica gel, for example Corasil, Nucleosil, Zorbax or Lichroprep is enclosed between two filters of sintered metal in the column. An inert filler, in this case glass beads, is provided on the filter in the conical part on the side of the upstream end of the column. The pre-column is connected to the coupling device shown in FIGS. 5–6 or in FIGS. 7–8. In the device shown in FIGS. 7–8 more pre-columns are used according to the invention. The device further comprises one or more separating columns which are preferably filled with the same type of carrier material. For conditioning the pre-columns and separating columns, conditioning liquid is rinsed through the columns and collected in a waste vessel. The precolumn is then loaded with the material to be chromatographed for example, a urine sample, by causing this material to flow through the pre-column which is connected to an outlet tube. After loading, the pre-column is connected to a separating column, after which the column is eluted. During this elution a so-called gradient elution is preferably used, which means that during the elution process the composition of the eluent is varied. The elution rate, i.e. the rate at which the eluent is pumped through the columns, depends on the dimensions of pre-column(s) and separating column(s), on the material to be chromatographed, the carrier material and the elution liquid. The elution is preferably carried out at room temperature; during the elution the pressure in the columns and coupling device may increase to 20 to 30 MPa, even to 40 MPa. The detection of the trace components may take place in various manners, for example, by means of spectroscopic methods such as UV-spectroscopy. In most of the cases, however, too many chromophorous "impurities" are present in the eluate to be able to successfully use a UV-measurement. Therefore preferably a radioactivity-measurement is used. In that case in metabolites examination, the chemical compound to be examined, usually a medicament, is labelled radioactive, for example with radioactive labelled carbon or hydrogen: $^{14}C$ or $^{3}H$. By measuring the emitted radioactivity, both the chemical compound itself and also possible metabolites thereof which comprise the labelled fragment, can be detected. This detection may take place "on-line" in the eluate flow, or "off-line", i.e. in the collected eluate fractions. The former method is more rapid, the "off-line" detection method usually gives more accurate results.

Figure 9:
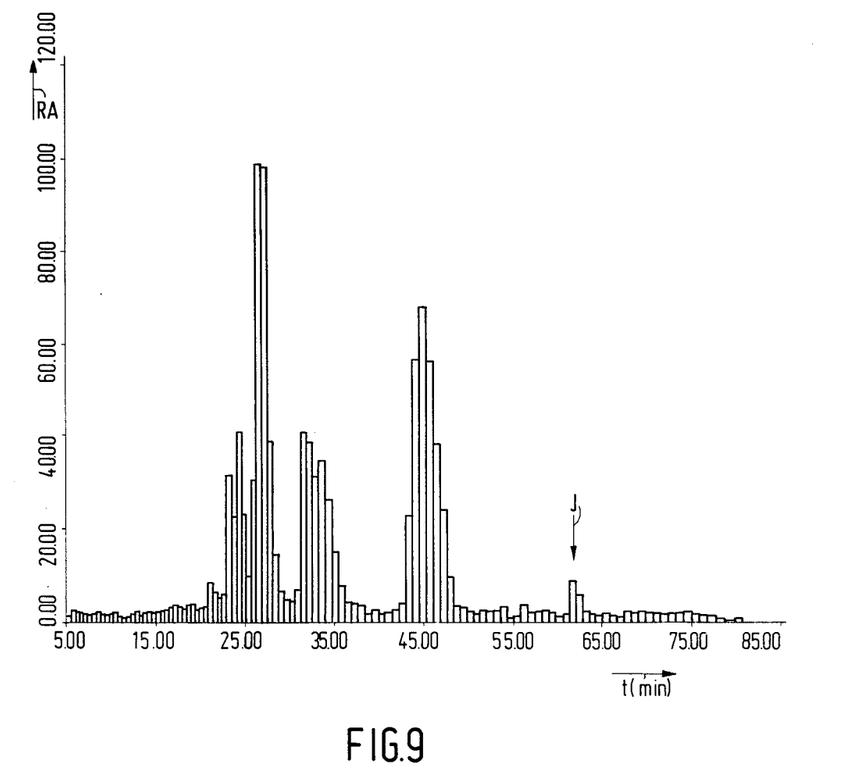

In order to be able to detect Isoxsuprine and metabolites hereof in urine, 200 ml of urine were subjected to the above-described chromatography process. Isoxsuprine or p-hydroxy-α-[1-{(1-methyl-2-phenoxyethyl)amino}ethyl]benzylalcohol is a substance having a vaso-dilating activity. The medicament and the metabolites hereof were present in traces in the sample to be chromatographed, namely in an overall quantity of a few micrograms. For the pre-concentration a stainless steel column according to the invention was used of the type as shown in FIG. 3 having a capacity of 27 ml. As a filler for the pre-column was used Nucleosil 30 C 8, a hydrophobated silica gel. The separating column had an inside diameter of 9 mm and a length of 50 cm, and was filled with Zorbax 7 C 8, also a hydrophobated silica gel. Isoxsuprine was labelled with $^{3}H$. The gradient elution was carried out with a mixture of water and methanol having a methanol content increasing from 0 to 100%. The elution rate was approximately 5 ml per minute. The trace components were detected off-line the chromatogram shown in FIG. 9 being obtained. In this chromatogram the measured radioactivity RA in counts per minute is plotted against time in minutes. The peak denoted in the chromatogram by I is of Isoxsuprine, the other peaks represent metabolites of Isoxsuprine.

Figure 10:
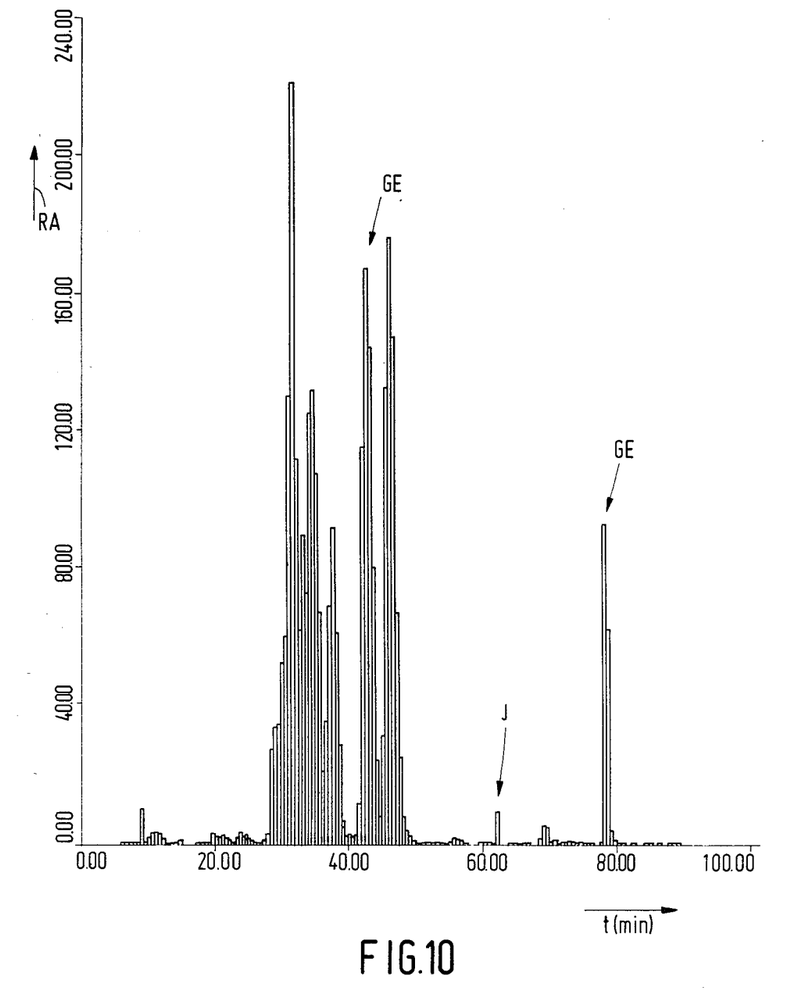

For comparison the above experiment was repeated with a straight pre-column usual for this purpose, instead of a pre-column according to the invention. The straight pre-column had an inside diameter of 9 mm which remains the same and a length of 15 cm. In practice a longer column could not be used because in that case during loading the pressure build-up in the column became too large. The experiment was further carried out with the same apparatus, the same type of material and in the same reaction conditions as described above for a pre-column according to the invention. The resulting chromatogram is shown in FIG. 10. It is clear from the chromatogram that so-called "ghost effects" occur: at GE.

Figure 5:
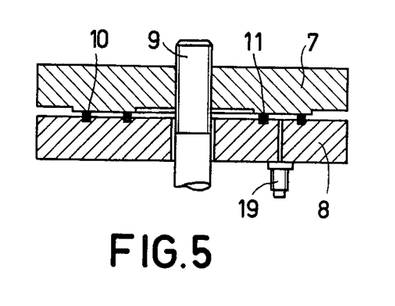
Figure 6:
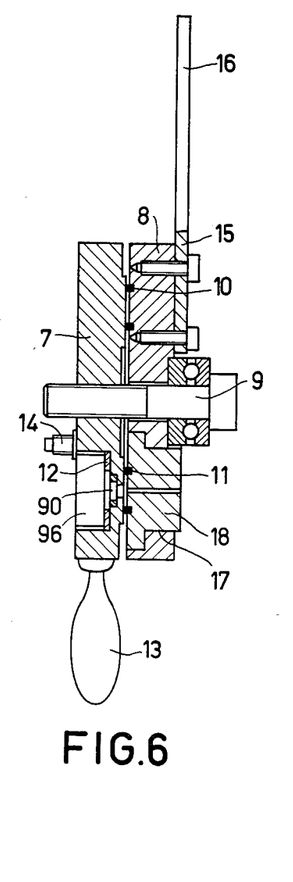

The pre-column according to the invention was also used in solving various other separating problems, as appears from the chromatograms shown in FIGS. 11, 12, 13 and 14. A single coupling device, as shown in FIGS. 4–6, or the six-fold device, as shown in FIGS. 7–8, was used.

Figure 11:
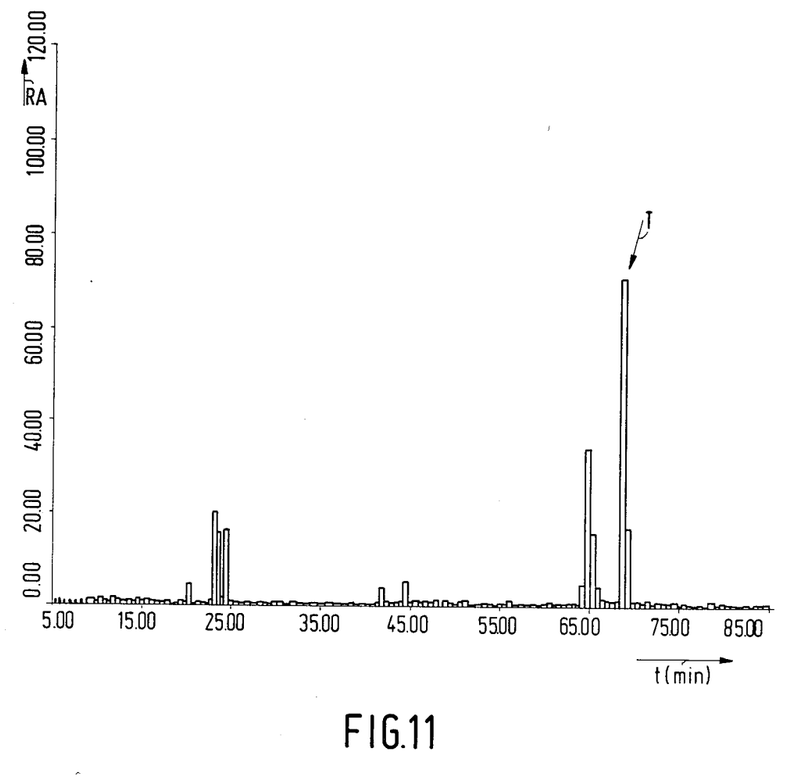
Figure 12:
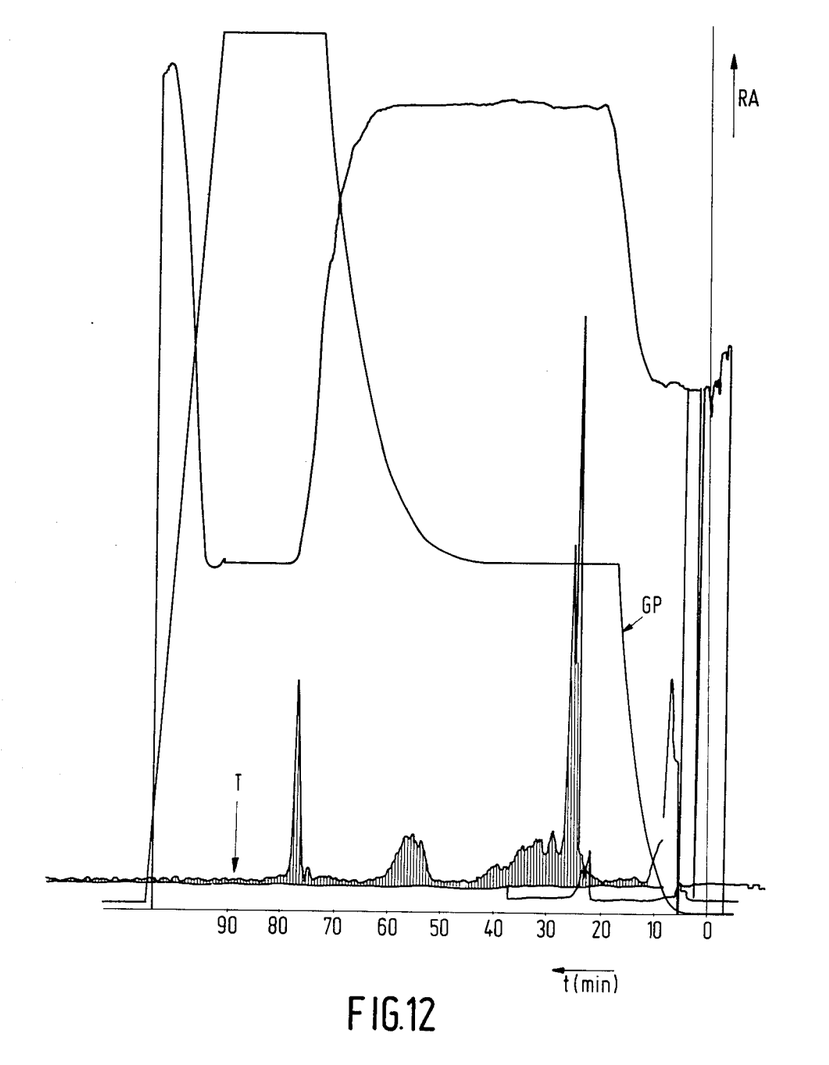

The chromatograms of FIGS. 11 and 12 have been obtained by column chromatography of samples which comprise [2-{4-(3-trifluoromethylphenyl)-1-piperazinyl}ethyl]-urea, a compound having antiagressive activity, and metabolites hereof. FIG. 11: stainless steel pre-column as shown in FIG. 2; capacity 1.5 ml; filler Nucleosil 30 C 8. Separating column: stainless steel; length 500 mm; inside diameter 9 mm; filler Nucleosil 7 C 8. Provided sample: 22 ml of blood plasma of a dog. Elution: gradient elution with a mixture of water and methanol having a methanol content increasing from 0 to 100%. The compound was labelled with $^{14}C$. Detection: off-line; measured radioactivity RA in counts per minute. The peak at T is of the active compound: the other ones are of metabolites. FIG. 12: stainless steel pre-column as shown in FIG. 3; capacity 27 ml; filler Nucleosil 7 C 8. Separating column: stainless steel; length 500 mm; inside diameter 9 mm; filler Nucleosil 7 C 8. Provided sample: 620 ml of urine of a dog. Elution: gradient elution with a mixture of water and methanol having a methanol content increasing from 0 to 100%. The compound was labelled with $^{14}C$: Detection: on-line. The peak at T is of the active compound; the other ones are of metabolites. The gradient profile of the eluent in % methanol is denoted by GP.

Figure 13:
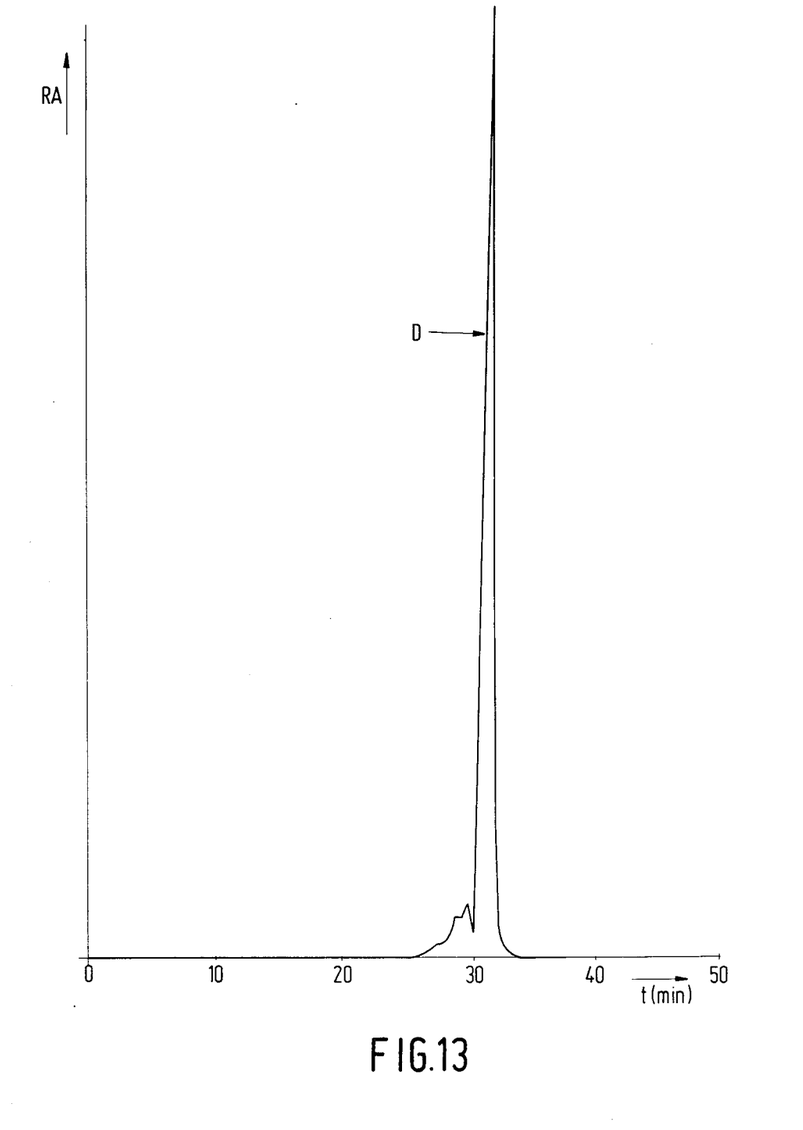

FIG. 13 shows a chromatogram obtained by chromatography of a urine sample to which 0.5 ppb of DES had been added. DES or diethylstilbestrol is a substance having oestrogenic activity. Stainless steel pre-column according to the invention having a capacity of 13 ml; filler Lichroprep RP2, a hydrophobated silica gel. Separating column: stainless steel; length 250 mm; inside diameter 9 mm; filler Nucleosil 7 C 8. Provided urine sample: 50 ml. Elution: gradient elution with water-methanol having a methanol content increasing from 0 to 100%.

DES was labelled with $^{3}H$. Detection: off-line. The peak at D is of DES.

Figure 14:
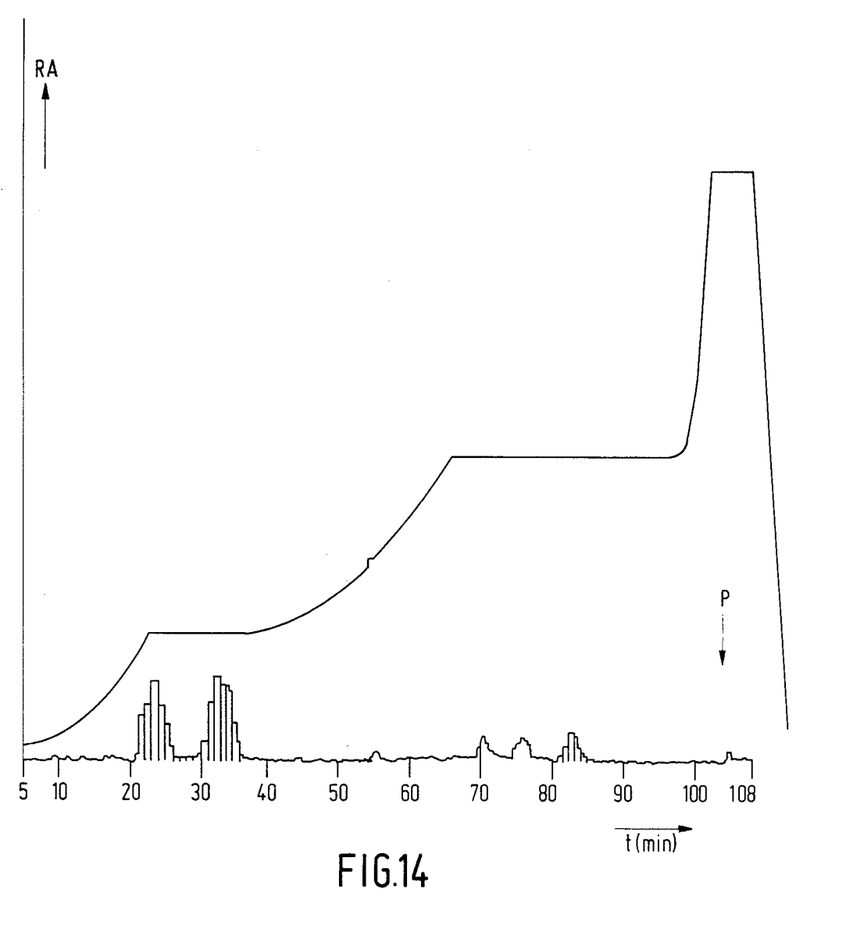

The chromatogram of FIG. 14 has been obtained by column chromatography of a urine sample of a rat containing traces of N-(2,6-difluorobenzoyl)-N'-(4-trifluoromethylphenyl) urea and metabolites hereof; this urea compound can be used as an insecticide in agriculture, horticulture and forestry. Stainless steel precolumn as shown in FIG. 3; capacity 27 ml; filler Nucleosil 30 C 8. Separating column: stainless steel; length 500 mm, inside diameter 9 mm; filler Zorbax 7 C 8. Provided urine sample: 121 ml. Elution: gradient elution with a mixture of water and methanol having a methanol content increasing from 0 to 100%.

The compound was labelled with $^{14}C$. Detection: on-line. The peak at P is of the active compound, the other ones are of metabolites. The gradient profile of the eluent in % methanol is denoted by GP.

We claim:

1. A pre-column of pressure-resistant material, to be used in connection with a separation column, for preconcentrating at elevated pressure substances to be chromatographed, which pre-column comprises a vessel-shaped body, having at its ends means for sealing connections, upstream with respect to an inlet tube for the liquid to be preconcentrated and downstream with respect to the separation column, and further having internally an upstream section converging towards the inlet tube for distributing the liquid to be preconcentrated over the internal cross-section of the body, and a preconcentration section, adapted to include a carrier material suited for preconcentration purposes, characterized in that said preconcentration section for the greater part converges toward the downstream end.

2. A pre-column as claimed in claim 1, further characterized in that the inner wall of the vessel-shaped body converges towards the downstream end conically.

3. A pre-column as claimed in claim 1, further characterized in that the inner wall of the vessel-shaped body converges more strongly in the direction of the upstream end than in the direction of the downstream end, and in that two filters are sealingly connected within the pre-column, one directly beneath the converging upstream section and the other beneath the converging preconcentration section close to the downstream end, which filters are adapted to enclose the carrier material, the former of said filters being in addition adapted to separate the carrier material from an inert filler provided in the converging upstream section.

4. A pre-column as claimed in claim 1, further characterized by including a separation column connected to the pre-column and in that the diameter of the downstream aperture of the vessel-shaped body is approximately equal to that of said separation column connected to the pre-column.

5. A pre-column as claimed in claim 1, further characterized in that the vessel-shaped body comprises two or more segments which are connected together in a pressure resistant manner.

6. A pre-column as claimed in claim 1, further characterized in that the pre-column has a resistance to pressure of approximately 40 MPa.

7. A pre-column as claimed in claim 5, further characterized in that the pre-column has a resistance to pressure of approximately 40 MPa.

8. A pre-column as claimed in claim 1, further characterized by including at least one separation column connected to the pre-column by means of a coupling member, said coupling member comprising two concentric disks which are rotatable relative to each other in a mutually sealing connection, one of the disks having apertures to which the pre-column and an inlet tube for liquid can sealingly connected, the other disk having apertures to which the separation column or columns and an outlet tube for waste liquid can be sealingly connected, the apertures in the two disks being adapted to communicate with each other at will by rotating one disk relative to the other.

9. A pre-column as claimed in claim 5, further characterized by including at least one separation column connected to the pre-column by means of a coupling member, said coupling member comprising two concentric disks which are rotatable relative to each other in a mutually sealing connection, one of the disks having apertures to which the pre-column and an inlet tube for liquid can be sealingly connected, the other disk having apertures to which the separation column or columns and an outlet tube for waste liquid can be sealingly connected, the apertures in the two disks being adapted to communicate with each other at will by rotating one disk relative to the other.

* * * * *